United States Patent [19]
Hudson

[11] Patent Number: 5,856,362
[45] Date of Patent: Jan. 5, 1999

[54] MEDICAMENTS FOR THE TREATMENT OF TOXOPLASMOSIS

[75] Inventor: Alan Thomas Hudson, Kent, England

[73] Assignee: Glaxo Wellcome Inc., Research Triangle Park, N.C.

[21] Appl. No.: 466,235

[22] Filed: Jun. 6, 1995

Related U.S. Application Data

[63] Continuation of Ser. No. 300,839, Sep. 2, 1994, abandoned.

[51] Int. Cl.$^6$ .................................................. A61K 31/12
[52] U.S. Cl. ............................................ 514/682; 568/328
[58] Field of Search .............................. 568/328; 514/682

[56] References Cited

U.S. PATENT DOCUMENTS

| | | | |
|---|---|---|---|
| 4,981,874 | 1/1991 | Latter et al. | 514/682 |
| 5,310,762 | 5/1994 | Latter et al. | 514/682 |

FOREIGN PATENT DOCUMENTS

| | | |
|---|---|---|
| 123238 | 10/1984 | European Pat. Off. . |

OTHER PUBLICATIONS

Hudson et al., Parasitology (1985) vol. 90, pp. 45–55.

*Primary Examiner*—Laura L. Stockton
*Attorney, Agent, or Firm*—Nixon & Vanderhye P.C.

[57] ABSTRACT

The present invention relates to the use of 2-[4-(4-chlorophenyl)cyclohexyl]-3-hydroxy-1,4-naphthoquinone or a physiologically acceptable salt or other physiologically funtional derivative thereof for the manufacture of a medicament for the treatment and/or prophylaxis of toxoplasmosis in animals, to pharmaceutical compositions for the treatment and/or prophylaxis of toxoplasmosis, comprising said compound as active ingredient and to a method of treating or preventing toxoplasmosis in an animal which comprises administering to said animal an effective amount of said compound.

6 Claims, No Drawings

MEDICAMENTS FOR THE TREATMENT OF TOXOPLASMOSIS

This is a continuation of application Ser. No. 08/300,839 filed on Sep. 2, 1994, now abandoned.

The present invention relates to the treatment of toxoplasmosis. More particularly the invention is concerned with the use of 2-[4-(4-chlorophenyl)cyclohexyl]-3-hydroxy-1,4-naphthoquinone and physiologically acceptable salts and physiologically functional derivatives thereof in treating toxoplasmosis, the use of said compound for the manufacture of medicaments for the treatment of toxoplasmosis, and novel dosage forms containing said compound.

*Toxoplasma gondii* is a parasitic organism which occurs in a wide range of animals, especially warm-blooded animals i.e. mammals, e.g. cattle, sheep, pigs, horses, dogs, cats and humans, and birds, e.g. poultry. In general this organism is considered to be non-pathogenic, and infection remains latent but in certain circumstances it can give rise to an acute illness (toxoplasmosis) which is often fatal. Thus, for example *T. gondii* is associated with serious disease in young children and in immunocompromised hosts. In particular, transplant patients are at risk from infection with *T. gondii* parasites introduced in the donated organ. In another group of immunocompromised patients, those with Acquired Immune Deficiency Syndrome (AIDS) toxoplasmosis is associated with life-threatening encephalitis. Other immunocompromised patients at risk include those being treated with immunosuppressive drugs in cancer chemotherapy.

Infection with *T. gondii* during early pregnancy may lead to foetal death or abnormality, whilst congenital infection during late pregnancy is associated with eye disease which may subsequently appear in early adulthood. In animal husbandry *T. gondii* frequently gives rise to foetal death in pregnant sheep. Felids (including the domestic cat) are the definitive hosts of *T. gondii* and a common source of human toxoplasmosis, via infective stages in the faeces.

Toxoplasmosis may be controlled to a certain extent using pyrimethamine together with a sulphonamide. However, at the present time no effective treatment for toxoplasmosis is available.

Hudson et al (Parasitology, 1985, 90, 45–55) have reported the testing of the following four hydroxynaphthoquinones against *Toxoplasma gondii*:

2-(8-cyclohexyloctyl)-3-hydroxy-1,4-naphthoquinone (menoctone);

2-(4-t-butylcyclohexyl)-3-hydroxy-1,4-naphthoquinone (BW58C);

2-(4-t-butylcyclohexylmethyl)-3-hydroxy-1,4-naphthoquinone (BW720C); and 2-(4-t-pentylcyclohexyl)-3-hydroxy-1,4-naphthoquinone (BW568C).

However, the results were considered to be "less promising" than those obtained against other organisms.

The compound 2-[4-(4-chlorophenyl)cyclohexyl]-3-hydroxy-1,4-naphthoquinone has previously been disclosed for example in European Patent No. 123,238 which relates to 2-substituted-3-hydroxy-1,4-naphthoquinones of formula (I)

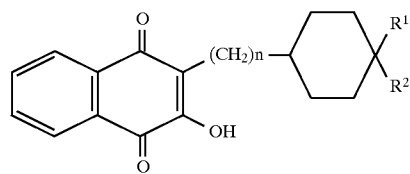

wherein either $R^1$ is hydrogen and $R^2$ is selected from $C_{1-6}$ alkoxy, aralkoxy, $C_{1-6}$ alkyl-$C_{1-6}$ alkoxy, phenyl substituted by one or two groups selected from halogen and $C_{1-6}$ alkyl, halogen and perhalo-$C_{1-6}$ alkyl or $R^1$ and $R^2$ are both $C_{1-6}$ alkyl or phenyl, and n is zero or 1, and physiologically acceptable salts thereof. The compounds said to have antiprotozoal activity. Specifically, compounds of formula (I) wherein n is zero are said to be active against the human malaria parasite *Plasmodium falcidarum* and also against Eimeria species such as *E. tenella* and *E. acervulina*, which are causative organisms of coccidiosis and compounds of formula (I) where n is 1 are said to be active against protozoa of the genus Theileria, in particular *T. annulata* or *T. parva*.

It has now surprisingly been found that the compound of formula (I) wherein n is zero, $R^1$ is hydrogen and $R^2$ is 4-chlorophenyl i.e. 2-[4-(4-chlorophenyl)cyclohexyl]-3-hydroxy-1,4-naphthoquinone, represented by formula (II):

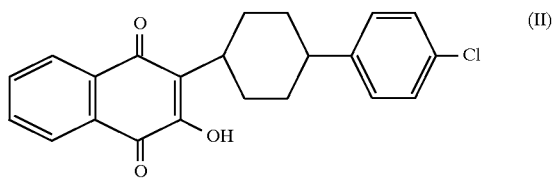

exhibits improved activity against *Toxoplasma gondii*.

Thus, in a first aspect the present invention provides the compound of formula (II) and physiologically acceptable salts and other physiologically functional derivatives thereof for use in the treatment and/or prophylaxis of toxoplasmosis in animals (including humans).

In another aspect the present invention provides the use of the compound of formula (II) and physiologically acceptable salts and other physiologically functional derivatives thereof for the manufacture of a medicament for the treatment and/or prophylaxis of toxoplasmosis in animals (including humans).

According to a further aspect the present invention provides a method of treating and/or preventing toxoplasmosis which comprises administering to an animal (including a human) suffering from or susceptible to toxoplasmosis an effective amount of a compound of formula (II), or a physiologically acceptable salt or other physiologically functional derivatives thereof.

Prevention of toxoplasmosis is particularly important in an immunocompromised host, as discussed hereinabove. In the case of immunosuppression resulting from HIV infection, prophylaxis may be required by those diagnosed as seropositive for HIV (i.e. having antibodies to HIV) and those with progressive generalised lymphadenopathy (PGL) or AIDS-related complex (ARC) as well as patients suffering from AIDS.

The hydroxyl group in the compound of formula (II) may form salts with appropriate bases, and physiologically acceptable salts of the compound (II) include inorganic base salts such as alkali metal (e.g. sodium and potassium) salts and alkaline earth metal (e.g. calcium salts; organic base salts e.g. phenylethylbenzylamine, dibenzylethylenediamine, ethanolamine and diethanolamine salts; and amino acid salts e.g. lysine and arginine.

Physiologically functional derivatives of formula (II) are derivatives which are converted in vivo, either by the host or the parasite to a compound of formula (II). Such derivatives include those of formula (III):

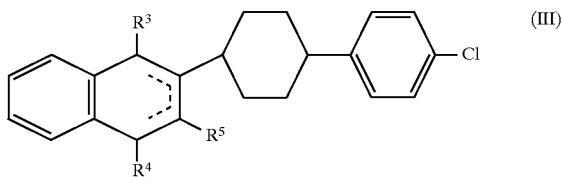

wherein
$R^3$ and $R^4$ each represent =O and the dotted line represents a double bond between the 2 and 3 positions of the quinone ring, in which case $R^5$ represents a group —$OCOR^6$; a group $OR^7$ or $SR^7$; or a group $NR^8R^9$, wherein $R^6$, $R^7$, $R^8$ and $R^9$ are as hereinbefore defined; or the dotted line represents double bonds at the 1,2 and 3,4 positions of the quinol ring and $R^3$, $R^4$ and $R^5$ each represents a group —$OCOR^{10}$, wherein $R^{10}$ represents an optionally substituted $C_{1-10}$ alkyl group.

It will be appreciated that the compound of formula (II) may exist as the cis or trans isomer, that is to say that the cyclohexyl ring may be cis or trans substituted by the naphthoquinone nucleus and the chlorophenyl group. Both cis and trans isomers and mixtures thereof in any ratio may be used in accordance with the present invention. In general when the compound is in the form of a mixture of isomers the trans isomer will be present in an amount of about 50% or will be the predominant isomer but the use of mixtures in which the cis isomer predominates is also included within the scope of the invention. The specific ratio of isomers may be varied as required; typical mixtures include those in which the cis/trans isomer ratio is about 1:1, 40:60 and 5:95. For use according to the present invention the trans isomer of the compound of formula (II), or a mixtures of its cis and trans isomers containing at least 95% e.g. 99% of the trans isomer, is preferred.

The compound of formula (II) may also exist in a tautomeric form in which the hydroxyl group donates its proton to one of the oxo groups and the use of such tautomeric forms is included within the scope of this invention. However, it is believed that the stable form is that shown in formula (II).

It will be appreciated that the amount of a compound of formula (II) or its salt or other physiologically functional derivative required for use in the treatment or prophylaxis of toxoplasmosis will depend inter alia on the route of administration, the age and weight of the mammal (e.g. human) to be treated and the severity of the condition being treated. In general, a suitable dose for administration to man for the treatment of toxoplasmosis is in the range of 1.0 mg to 200 mg per kilogram bodyweight per day, for example from 5 mg/kg to 100 mg/kg, particularly 25 to 100 mg/kg. It will be appreciated that for administration to neonates, lower doses may be required.

For prophylactic treatment the compound of Formula (II) or a physiologically acceptable salt or other physiologically functional derivative thereof may also be given less frequently, e.g. as a single dose on alternate days, once or twice per week or once or twice per month. The dosage for prophylactic treatment will depend inter alia on the frequency of administration, and, where a depot preparation or controlled release formulation is used the rate of release of the active ingredient. Thus for once-weekly administration a suitable prophylactic dose is in the range 0.5 to 100 mg/kg, e.g. 1.0 to 50 mg/kg particularly 5 to 50 mg/kg.

It should be understood that the dosages referred to above are calculated in terms of the compound of formula (II) per se.

For use according to the present invention the compound of formula (II) or a physiologically acceptable salt or other physiologically functional derivative thereof is preferably presented as a pharmaceutical formulation.

Pharmaceutical formulations comprise the active ingredient (that is, the compound of formula (II) or a physiologically acceptable salt or other physiologically functional derivative thereof) together with one or more pharmaceutically acceptable carriers thereof and optionally other therapeutic and/or prophylactic ingredients. The carrier(s) must be acceptable in the sense of being compatible with the other ingredients of the formula and not deleterious to the recipient thereof.

The compound of formula (II) or its salt or other physiologically functional derivative may conveniently be presented as a pharmaceutical formulation in unit dosage form. A convenient unit dose formulation contains the active ingredient in an amount of from 10 mg to 3 g, e.g. 50 mg to 3 g. A typical unit dose may contain for example 50 mg, 1 g, 2 g or 3 g of the active ingredient.

Pharmaceutical formulations include those suitable for oral, topical (including dermal, buccal and sublingual), rectal and parenteral (including subcutaneous, intradermal, intramuscular and intravenous), administration as well as administration by naso-gastric tube. The formulation may, where appropriate, be conveniently presented in discrete dosage units and may be prepared by any of the methods well known in the art of pharmacy. All methods include the step of bringing into association the active ingredient with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of the active ingredient. A tablet may be made by compression or moulding, optionally with one or more accessory ingredients. Compressed tablets may be prepared by compressing in a suitable machine the active compound in a free-flowing form such as a powder or granules optionally mixed with a binder, lubricant, inert diluent, lubricating agent, surface-active agent or dispersing agent. Moulded tablets may be made by moulding an inert liquid diluent. Tablets may be optionally coated and, if uncoated, may optionally be scored. Capsules may be prepared by filling the active ingredient, either alone or in admixture with one or more accessory ingredients, into the capsule shells and then sealing them in the usual manner. Cachets are analogous to capsules wherein the active ingredient together with any accessory ingredient(s) is sealed in a rice paper envelope. The compound of formula (II) or a physiologically acceptable salt or other physiologically functional derivative thereof may also be formulated as dispersible granules, which may for example be suspended in water before administration, or sprinkled on food. The granules may be packaged e.g. in a sachet. Formulations suitable for oral administration wherein the carrier is a liquid may be presented as a solution or a suspension in an aqueous liquid or a non-aqueous liquid, or as an oil-in-water liquid emulsion.

Formulations for oral administration include controlled release dosage forms e.g. tablets wherein the active ingredient is formulated in an appropriate release—controlling matrix, or is coated with a suitable release—controlling film. Such formulations may be particularly convenient for prophylactic use.

The active ingredient may also be formulated as a solution or suspension suitable for administration via a naso-gastric tube. Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active compound with the softened or melted carrier(s) followed by chilling and shaping in moulds.

Pharmaceutical formulations suitable for parenteral administration include sterile solutions or suspensions of the active compound in aqueous or oleaginous vehicles. Injectible preparations may be adapted for bolus injection or continuous infusion. Such preparations are conveniently presented in unit dose or multi-dose containers which are sealed after introduction of the formulation until required for use. Alternatively, the active ingredient may be in powder form which is constituted with a suitable vehicle, such as sterile, pyrogen-free water, before use.

The compound of formula (II) or a physiologically acceptable salt or other physiologically functional derivative thereof may also be formulated as a long-acting depot preparation, which may be administered by intramuscular injection or by implantation e.g. subcutaneously or intramuscularly. Depot preparations may include, for example, suitable polymeric or hydrophobic materials, or ion-exchange resins. Such long-acting formulations are particularly convenient for prophylactic use.

It should be understood that in addition to the aforementioned carrier ingredients the pharmaceutical formulations for the various routes of administration described above may include, as appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

The compound of formula (II) or a physiologically acceptable salt or other physiologically functional derivative thereof may also be used in accordance with the present invention in combination or concurrently with other therapeutic agents, for example agents used in the treatment of immunocompromised patients, including antibacterial agents; antifungal agents; anticancer agents such as interferons e.g. alpha-interferon; antiviral agents such as azidothymidine (AZT, zidovudine); immunostimulants and immunodulators. The compound of formula (II) may also be administered in combination with a 4-pyridinol compound, as described in EPA 123,239 e.g. 3,5-dichloro-2,6-dimethylpyridinol (meticlorpindol).

Compositions suitable for veterinary use include those adapted for oral, parenteral, and intrarumenal administration.

Compounds suitable for oral administration include drenches (oral liquid dosing), which may be solutions or suspensions; tablets, boluses, pastes, or in-feed preparations in the form of powders, granules or pellets.

Alternatively, veterinary compositions may be adapted to be administered parenterally by sub-cutaneous, intramuscular or intravenous injection of a sterile solution or suspension, by implantation or as an intramammary injection whereby a suspension or solution is introduced into the udder via the teat.

For intrarumenal injection, the compositions of the invention may be solutions or solid or microcapusule suspensions. Typically the compositions are similar to the oral liquid preparations or parenteral preparations described herein. Such compositions are injected directly into the rumen, usually through the side of the animal, for example by a hypodermic syringe and needle or by an automatic injection device capable of giving single or multiple doses.

For veterinary administration the compound of formula (II) or its salt or other physiologically functional derivative is preferably formulated with one or more veterinarily acceptable carriers.

For oral administration, fine powders or granules may contain diluting agents, for example lactose, calcium carbonate, calcium phosphate, mineral carriers, etc., dispersing and/or surface active agents, for example polysorbates such as Tweens or Spans, and may be presented in a drench, in water or in a syrup, in a bolus, paste, or in a feed preparation, in capsules or sachets in the dry state or in a non-aqueous suspension, or in a suspension in water or syrup. Where desirable or necessary, preserving, suspending, thickening or emulsifying agents can be included. If intended for oral use, a bolus will be provided with retention means to inhibit regurgitation, for example it may be weighted with a heavy density material such as iron or tungsten or the like or may be retained by its shape, for example by wings which spring after administration. Boluses may contain disintegrating agents such as maize starch or calcium or sodium methyl celluloses, hydroxypropylmethylcellulose, guar based vegetable gums, sodium alginates or sodium starch glycolates; granulating or binding agents such as starch in the form of mucilage, starch derivatives, such as "Snow Flake", cellulose derivatives such as talc, calcium stearate, methyl cellulose, gelatin or polyvinylpyrrolidone; and/or lubricating agents, such as magnesium stearate or stearic acid.

For parenteral administration, the compounds may be presented in sterile injection solutions which may contain antioxidants or buffers, or as injectable suspensions. Suitable solvents include water, in the case of suspensions, and organic solvents such as dimethylformamide, dimethylacetamide, diethylacetamide, ethyl lactate, ethyl akate, dimethylsulphoxide, alchols, e.g. ethanol, glycols, e.g. ethylene glycol, propylene glycol, butylene glycol and hexamethylene glycol, polyethylene glycols containing 2 to 159 ethylene glycol monomer units and having average molecular weights from about 90 to 7500, glycerin formal, glycofural, glycerol, isopropylmyristate N-methylpyrrolidone, 2-pyrrolidone polyethylene glycoethers of tetrahydrofurfuryl alcohol and diethylene glycol, and fixed and neutral oils, for example fractionated coconut oil. Parenteral formulations may also contain isotonic agents.

For veterinary use the compound of formula (II) may be employed together with other therapeutic agents used in the field of animal health, for example with anticoccidial and/or antitheilerial agents.

Methods for preparing the compound of formula (II) are described in EP 123,238, and one specific method is illustrated in example 3.

The following examples illustrate, with reference to the compound of formula (II) pe se, pharmaceutical and veterinary formulations which may be employed in accordance with the present invention:

Injectable solution

A solution for intramuscular injection may be prepared by mixing:

| | |
|---|---|
| Compound of formula (II) | 9.5 parts by weight |
| Dimethyl sulphoxide | 19.0 parts by weight |
| Sorbitan monooleate | 4.5 parts by weight |
| Corn oil | 67.0 parts by weight |
| | 100.0 |

Injectable solution

The following injectable formulation was prepared:

| | |
|---|---|
| Compound of formula (II) | 5 parts by weight |
| N-methyl-pyrollidone | 48.3 parts by weight |
| Tween 80 | 2 parts by weight |
| Span 80 | 4.7 parts by weight |
| Miglyol 812 | 40 parts by weight |
| | 100.0 |

Tablet

| | |
|---|---|
| Compound of formula (II) | 25.0 mg |
| Lactose BP | 48.5 mg |
| Microcrystalline Cellulose BP ("Avicel pH 101") | 10.0 mg |
| Low-substituted Hydroxypropyl; Cellulose BP ("LHPC LH-11") | 10.0 mg |
| Sodium Starch Glycollate BP ("Explotab") | 3.0 mg |
| Povidone BP ("K30") | 3.0 mg |
| Magnesium Stearate BP | 0.5 mg |
| | 100.0 mg |

Oral suspension

| | |
|---|---|
| Compound of formula (II) | 50 mg |
| Avicel RC 591 | 75 mg |
| Sucrose syrup | 3.5 ml |
| Methylhydroxybenzoate | 5 mg |
| Colour | 0.01% w/v |
| Cherry flavour | 0.1% v/v |
| Tween 80 | 0.2% v/v |
| Water | to 5 ml |

Injectable suspension

| | |
|---|---|
| Compound of formula (II) | 100 mg |
| Polyvinyl pyrrolidone (PVP) | 170 mg |
| Tween 80 | 0.2% v/v |
| Methylhydroxybenzoate | 0.1% w/v |
| Water for Injection | to 3 ml |

Capsule

| | |
|---|---|
| Compound of formula (II) | 100 mg |
| Starch 1500 | 150 mg |
| Magnesium stearate | 2.5 mg |
| filled into a hard gelatin capsule | |

Aqueous Suspension

An aqueous suspension may be prepared as follows:

| | |
|---|---|
| Compound of formula (II) | 1.00 part by weight |
| Neosyl | 16.00 parts by weight |
| Bentonite | 3.20 parts by weight |
| Glycerin | 15.00 parts by weight |
| Sodium benzoate | 1.00 part by weight |
| Bevaloid 35/2 | 1.00 part by weight |
| Thymol | 0.04 parts by weight |
| Water | 62.76 parts by weight |
| | 100.00 |

Salt Block

A salt block may be prepared by mixing a finely divided compound of formula (II) (0.5 parts by weight) with sodium chloride (99.5 parts by weight) and the mixture pressed into blocks.

Paste

The following paste may be prepared:-

| | |
|---|---|
| Compound of formula (II) | 3.0 parts by weight |
| Gum tragacanth | 4.0 parts by weight |
| Bevaloid 35/3 | 1.0 part by weight |
| Nipagin "M" | 0.1 parts by weight |
| Glycerin | 19.0 parts by weigt |
| Water | 72.9 parts by weight |
| | 100.00 |

Biological Test Results

EXAMPLE 1

Method:

Male CD-1 mice were infected subcutaneously (s.c.) with 200 organisms of the Collier strain of *Toxoplasma gondii*. Drugs, in the form of a 0.25% aqueous celacol solution or suspension, were daily dosed orally (p.o.) at 50 mg/kg, beginning on the day of infection and continuing for 15 days. Animals were then kept for a further 15 days. The time to death was noted for each individual mouse. The mean time to death, together with one standard deviation, was recorded for combined groups, each of 5 mice, tested on at least two separate occasions for each naphthoquinone.

Results

| Compound | Mean time to death |
|---|---|
| Compound (II) | 25.5 (± 4.3) |
| Untreated controls | 9.84 ± 0.60 |
| BW58C[1] | 14.05 ± 1.67 |
| BW568C[2] | 15.05 ± 2.05 |
| BW720C | 11.09 ± 0.60 |
| Menoctone | 18.85 ± 3.00 |

1. Trans isomer
2. Cis/trans ratio = 1:1

EXAMPLE 2

Groups of 10 female SW mice weighing ca. 20 g each were infected intraperitoneally with $2\times10^3$ trophozoites obtained from the peritoneal cavity of previously infected mice. The compound of the invention in the form of a 0.25% aqueous solution or suspension was administered to the treatment groups by gavage. The groups were dosed respectively at 20, 50 and 100 mg/kg/day in a single dose, for 15 days beginning 24 hours after infection with *T. gondii*.

Control groups were infected as described above but not treated.

Results

| | Percent mortality on day* | | | |
|---|---|---|---|---|
| Treatment | 7 | 8 | 15 | 20 |
| Untreated controls | 30 | 100 | | |
| Test compound (20 mg/kg/day) | 10 | 20 | 20 | 20 |
| Test compound (50 mg/kg/day) | 0 | 10 | 10 | 10 |
| Test compound (100 mg/kg/day) | 10 | 10 | 10 | 10 |

*after infection.

EXAMPLE 3

2-[trans-4-(4-Chlorophenyl)cyclohexyl]-3-hydroxy-1,4-naphthoquinone a) 4-(4-Chlorophenyl)cyclohexane-1-carboxylic Acid Acetyl chloride (30 g) and finely powdered aluminium chloride (60 g) were stirred together in carbon disulphide (120 ml) and then cooled to −50° C., in a $CO_2$/oxitol bath. Cyclohexene (30 g), previously cooled to −50° C., was added dropwise during 10 minutes while maintaining the temperature of the reaction mixture at below −20° C. The mixture was stirred at −50° C. for a further 60 minutes and the solvent then decanted to leave a gummy orange complex. A little chlorobenzene was added as the material warmed to ambient temperature; the remainder of the chlorobenzene (total 300 ml) was then added, the so-obtained solution heated at 40° C. for 3 hours with stirring, poured onto a mixture of ice and concentrated hydrochloric acid and the organic layer separated, washed with 2M hydrochloric acid, 2M sodium hydroxide and water, dried over anhydrous sodium sulphate and evaporated to dryness. The product was distilled in vacuo, the fraction boiling at 140°–154° C. (0.1 mm Hg) collected, diluted with an equal volume of petroleum ether (40–60), cooled to −6° C. and a continuous stream of nitrogen gas bubbled through, and the separated colourless solid recovered.

Bromine (2.8 ml) was added to a solution of sodium hydroxide (6.2 g) in water (42 ml) at 0° C. The above-obtained substituted hexahydroacetophenone (3.1 g) was dissolved in dioxan (15 ml) and the cold hypobromite solution then added, keeping the reaction mixture at below 20° C. The reaction mixture was stirred at ambient temperature for 6 hours then allowed to stand overnight. Sodium metabisulphite was added to destroy excess hypobromite, the mixture cooled and then acidified to give a colourless solid. The solid was filtered off, washed with water, dried and recrystallised from ethanol to give 4-(4-chlorophenyl) cyclohexane-1-carboxylic acid, m.p. 254°–256° C.

b) 2-[4-(4-chlorophenyl)cyclohexyl]-3-chloro-1,4-naphthoquinone

A mixture of 2-chloro-1,4-naphthoquinone (3.95 g, 0.02 mol), 4-(4-chlorophenyl)cyclohexane-1-carboxylic acid (4.9 g, 0.02 mol) and powdered silver nitrate (1.05 g, 0.0062 mol) was heated to reflux with vigorous stirring in 40 ml of acetonitrile. A solution of ammonium persulphate (12.0 g, 0.0525 mol) in 50 ml of water was added dropwise over 1 hour. The mixture was refluxed for 3 hours then cooled in ice for 30 mins, after which it was filtered, and the residual sticky solid extracted twice with boiling chloroform to remove inorganic material. The chloroform was removed by evaporation to leave a yellow-brown solid (ca 2.7 g). This was dissolved in 40 ml of boiling acetonitrile; a little insoluble material was removed by filtration. On cooling, the title compound separated as yellow crystals, (550 mg) m.p. 172°–175° C.

NMR, $\delta H(d_6$-DMSO) 8.05 (2H, mult., β-naphth), 7.85 (2H, mult., α-naphth), 7.30 (4H, s., PhH), 3.30 (1H, br.t., CH), 2.67 (1H, br.t., CH), 1.2–2.4 (8H, mult., 4×$CH_2$).

c) 2-[4-(4-chlorophenyl)cyclohexyl]-3-hydroxy-1,4-naphthoquinone

The product of stage (b) was suspended in 10 ml of boiling methanol and 0.55 g of potassium hydroxide in 5.5 ml of water was added dropwise over 15 mins. The mixture was refluxed until a dark red solution formed, (after ca. 6 hrs) when 2 ml of concentrated hydrochloric acid was cautiously added dropwise. The mixture was cooled and filtered, and the solid residue washed thoroughly with water. The water washings were re-acidified and filtered. The combined solid residues (500 mg) mp 200°–209°, were recrystallised from acetonitrile to give the title product as the trans-isomer (300 mg) m.p. 216°–219° C.

I claim:

1. A method of treating toxoplasmosis in an animal which comprises administering to said animal suffering from toxoplasmosis an effective treatment amount of 2-[4-(4-chlorophenyl)cyclohexyl]-3-hydroxy 1,4-naphthoquinone or a physiologically acceptable salt thereof.

2. A method according to claim 1 wherein the compound 2-[trans-4-(4-chlorophenyl)-3-hydroxy-1,4-naphthoquinone is administered.

3. A method according to claim 1 or claim 2 wherein the compound or a physiologically acceptable salt thereof is administered in an amount of from 25 to 100 mg per kilogram of animal bodyweight per day.

4. A method according to claim 1 wherein the animal is a human.

5. A method according to claim 4 wherein the human is immunocompromised.

6. A method according to claim 5 wherein the human has an HIV infection.

* * * * *